(12) United States Patent
Kesselgruber et al.

(10) Patent No.: US 7,491,671 B2
(45) Date of Patent: Feb. 17, 2009

(54) PHOSPHOLANE SALTS AND THEIR USE IN ENANTIOSELECTIVE HYDROGENATION

(75) Inventors: Martin Kesselgruber, Basel (CH); Marc Thommen, Nuglar (CH)

(73) Assignee: Solvias AG, Basel (CH)

( * ) Notice: Subject to any disclaimer, the term of this patent is extended or adjusted under 35 U.S.C. 154(b) by 346 days.

(21) Appl. No.: 10/556,084

(22) PCT Filed: May 7, 2004

(86) PCT No.: PCT/EP2004/050732

§ 371 (c)(1), (2), (4) Date: Nov. 9, 2005

(87) PCT Pub. No.: WO2004/098772

PCT Pub. Date: Nov. 18, 2004

(65) Prior Publication Data

US 2007/0015925 A1 Jan. 18, 2007

(30) Foreign Application Priority Data

May 9, 2003 (CH) ..................................... 0813/03

(51) Int. Cl.
*B01J 31/00* (2006.01)
(52) U.S. Cl. ......................................... 502/162; 556/21
(58) Field of Classification Search .................. 502/162; 556/21

See application file for complete search history.

(56) References Cited

U.S. PATENT DOCUMENTS

| 5,874,600 | A * | 2/1999 | Rautenstrauch et al. ..... 556/136 |
| 6,583,312 | B2 * | 6/2003 | Sirges et al. ................. 560/179 |
| 6,632,953 | B1 | 10/2003 | Stürmer et al. | |
| 6,706,926 | B1 | 3/2004 | Brown et al. | |
| 6,750,171 | B2 * | 6/2004 | Hoge et al. .................. 502/162 |
| 2004/0133042 | A1 | 7/2004 | Brown et al. | |

FOREIGN PATENT DOCUMENTS

| WO | 99/62917 | 12/1999 |
| WO | 00/26220 | 5/2000 |

OTHER PUBLICATIONS

Jens Holz et al., "Synthesis of Chiral 2,5-Bis(oxymethyl)-Functionalized Bis(phospholanes) and Their Application in Rh- and Ru-Catalyzed Enantioselective Hydrogenations", European Journal of Organic Chemistry, vol. 4624, No. 24, pp. 4615-4624, Dec. 2001, XP002303790, ISSN: 1434-193.

Mark J. Burk et al., "Bis(phospholane) Ligands Containing Chiral Backbones. Matching and Mismatching Effects in Enantioselective Hydrogenation of α-Keto Esters", Organometallics, vol. 19, No. 3, pp. 250-260, Feb. 7, 2000, XP002195095, ISSN: 0276-7333.
Duncan Carmichael et al., "Hybrid P-chiral diphosphines for asymmetric hydrogenation", Chemical Communications, No. 3, pp. 261-262, 1999, XP001069478, ISSN: 1359-7345.
Jens Holz et al., "Synthesis of a New Class of Functionalized Chiral Bisphospholane Ligands and the Application in Enantioselective Hydrogenations", Journal of Organic Chemistry, vol. 63, No. 22, pp. 8031-8034, Oct. 30, 1998, XP002130689, ISSN: 0022-3263.
Mark J. Burk et al., "Preparation and Use of $C_2$-Symmetric Bis(phospholanes): Production of α-Amino Acid Derivatives via Highly Enantioselective Hydrogenation Reactions", Journal of the American Chemical Society, vol. 115, pp. 10125-10138, 1993, XP000926475, ISSN: 0002-7863.
Konstantin W. Kottsieper et al., "Synthesis of enantiopure $C_1$ symmetric diphosphines and phosphino-phosphonites with *ortho*-phenylene backbones", Tetrahedron: Asymmetry, vol. 12, No. 8, pp. 1159-1169. May 21, 2001, XP004245864, ISSN: 0957-4166.
Wenge Li et al., "Synthesis of Chiral Hydroxyl Phospholanes from D-mannitol and Their Use in Asymmetric Catalytic Reactions", Journal of Organic Chemistry, vol. 65, pp. 3489-3496, 2000, XP001069473, ISSN: 0022-3263.
T.V. RajanBabu et al., "Synthesis, Characterization, and Applicability of Neutral Polyhydroxy Phospholane Derivatives and Their Rhodium(I) Complexes for Reactions in Organic and Aqueous Media", Journal of the American Chemical Society, vol. 123, No. 42, pp. 10207-10213, Oct. 24, 2001, XP002303791, ISSN: 0002-7863.
Daniel A. Dobbs et al., Industrial Synthesis of (+)-*cis*-Methyl Dihydrojasmonate by Enantioselective Catalytic Hydrogenation; Identification of the Precatalyst [Ru((−)-Me-DuPHOS)(H)-($\eta^6$-1,3,5-cyclooctatriene)](BF$_4$), Angewandte Chemie, International Edition, vol. 39, No. 11, pp. 1992-1995, Jun. 2, 2000, XP002303792, ISSN: 0570-0833.
Mark J. Burk, "$C_2$ -Symmetric Bis(phospholanes) and Their Use in Highly Enantioselective Hydrogenation Reactions", Journal of American Chemical Society, vol. 113, pp. 8518-8519, 1991, XP002065437, ISSN: 0002-7863.

* cited by examiner

*Primary Examiner*—Rei-tsang Shiao
(74) *Attorney, Agent, or Firm*—Wenderoth, Lind & Ponack, L.L.P.

(57) ABSTRACT

Process for preparing a catalyst solution by reacting metal complexes and diphosphines in the presence of an inert organic solvent, which is characterized in that a) an uncharged or cationic metal complex having a TM8 metal as central atom, and b) a salt of a chiral ditertiary diphosphine which has one or two phospholane groups which are bound to a carbon chain having from 2 to 4 carbon atoms and contain anions selected from the group consisting of $R_C COO^-$, $R_C SO_3^-$, $BF_4^-$, $PF_6^-$, $AsF_6^-$, $SbF_6^-$, $B(C_6F_5)_4^-$ and $B(3,5$-bistrifluoromethylphenyl)$_4^-$, are reacted with one another, where the ratio of the components a) and b) is from 1:1 to 1:2 and $R_C$ is $C_1$-$C_6$-haloalkyl, $C_5$-$C_{10}$-halocycloalkyl or $C_6$-$C_{10}$-haloaryl.

7 Claims, No Drawings

PHOSPHOLANE SALTS AND THEIR USE IN ENANTIOSELECTIVE HYDROGENATION

This application is a 371 of PCT/EP04/50732 filed on May 7, 2004.

The present invention relates to phospholane salts, to a process for preparing catalyst solutions by complexation of catalyst precursors using these phospholane salts as ligands and to the use of the catalyst solutions prepared in this way in the asymmetric catalyzed hydrogenation of heteroatom-carbon and C=C double bonds.

An important class of ligands for asymmetric, in particular rhodium-catalyzed hydrogenation are chiral C2-symmetric bisphospholanes, e.g. 1,2-bis(2,5-dimethylphospholanyl)benzene as representatives of the DuPHOS family, 1,2-bis(2,5-dimethylphospholanyl)ethane (BPE) (Burk, M. J. et al., J. Am. Chem. Soc. 1991, 113, 8518), and, for example, 1,2-bis[3,4-bis(benzyloxy)-2,5-dimethylphospholanyl]ethane as representatives of the RoPHOS family (Holz, J. et al., J. Org. Chem. 1998, 63, 8031). Monophospholanes which have a tertiary phosphine radical are also known (Kottsieper, K. W. et al, Tetrahedron: Asymmetry 2001, 12, 1159). For the purposes of the present invention, phospholanes are aliphatic, five-membered, heterocyclic compounds having a phosphorus atom in the ring.

While a few phospholanes of the abovementioned families, e.g. DuPhos (Burk et al., J. Am. Chem. Soc. 1993, 115, 10125), form crystalline, air-stable compounds, most of these compounds are obtained in liquid form. Many of the solid and liquid forms are strongly hygroscopic and very sensitive to oxidation, so that in air these phospholanes are quickly decomposed by oxidation. The handling and storage of these phospholanes is therefore made difficult by their consistency and their high air sensitivity.

Catalyst complexes with phospholane ligands are essentially preformed and, if appropriate, purified, since in-situ preparation forms complex mixtures by means of which it is not possible to achieve reproducible results. However, in-situ preparation gives processing and economic advantages.

Phospholanes can also be present in the form of their salts: the preparation of a DuPHOS-analogous diphosphine in the form of a salt (phosphonium dihydrochloride) is described by Kottsieper (Kottsieper, K. W. et al., Tetrahedron: Asymmetry 2001, 12, 1159). This compound is strongly hygroscopic. Also known are RoPHOS phosphonium salts (with methanesulfonate as counterion) which were firstly prepared by Zhang et al. without being recognized (Zhang, X. et al., J. Org. Chem. 2000, 65, 3489) and were later identified as the abovementioned salts (RajanBabu, T. V. et al., J. Am. Chem. Soc. 2001, 123, 10207). However, these compounds, too, are very hygroscopic and unstable in air.

Ru complexes have also been prepared in-situ. Here, the reaction of an equimolar solution of [Ru(1,2:5,6-η-1,5-cyclooctadiene)(η$^3$-methallyl)$_2$] and 1,2-bis-(2,5-dimethylphospholanyl)benzene with one equivalent of HBF$_4$.Et$_2$O and catalytical amounts of BF$_3$.Et$_2$O gave mixtures of precatalysts (Dobbs, D. A. et al., Angew. Chem. 2000, 112, 11, 2080).

It has now surprisingly been found that certain salts of ditertiary diphosphines having one or two phospholane groups are suitable for the in-situ preparation of metal complexes as homogeneous hydrogenation catalysts which ensure uniform reaction conditions. It has also been found that salt formation frequently forms solids which are not hygroscopic or only slightly hygroscopic and insensitive to oxidation in air, as a result of which handleability, storage and transport can be improved considerably.

The invention accordingly provides, firstly, a process for preparing a catalyst solution by reacting metal complexes and diphosphines in the presence of an inert organic solvent, which is characterized in that a) an uncharged or cationic metal complex having a TM8 metal as central atom, and b) a salt of a chiral ditertiary diphosphine which has one or two phospholane groups which are bound to a carbon chain having from 2 to 4 carbon atoms and contain anions selected from the group consisting of R$_c$COO$^-$, R$_c$SO$_3^-$, BF$_4^-$, PF$_6^-$, AsF$_6^-$, SbF$_6^-$, B(C$_6$F$_5$)$_4^-$ and B(3,5-bistrifluoromethylphenyl)$_4^-$, are reacted with one another, where the ratio of the components a) and b) is from 1:1 to 1:2 and R$_c$ is C$_1$-C$_8$-haloalkyl, C$_5$-C$_{10}$-halocycloalkyl or C$_8$-C$_{10}$-haloaryl.

The component a) can be a salt or uncharged or cationic metal complex, as is known from the literature and is described, for example, in "Catalytic asymmetric synthesis" (Editor I. Ojima, VCH, 1993), "Asymmetric catalysis in organic synthesis" (R. Noyori, Wiley, 1994), and "Transition metals for organic synthesis" (Editor M. Beller, C. Bolm, Wiley-VCH, 1998).

Suitable inert solvents are, for example, aliphatic, cycloaliphatic and aromatic hydrocarbons (pentane, hexane, heptane, petroleum ether, cyclohexane, methylcyclohexane, benzene, toluene, xylene), halogenated aliphatic hydrocarbons (methylene chloride, chloroform, dichloroethane and tetrachloroethane), nitriles (acetonitrile, propionitrile, benzonitrile), ethers (diethyl ether, dibutyl ether, t-butyl methyl ether, ethylene glycol dimethyl ether, ethylene glycol diethyl ether, diethylene glycol dimethyl ether, tetrahydrofuran, dioxane, diethylene glycol monomethyl or monoethy ether), ketones (acetone, methyl isobutyl ketone), carboxylic esters and lactones (ethyl or methyl acetate, valerolactone), N-substituted lactams (N-methylpyrrolidone), carboxamides (dimethylacetamide, dimethylformamide), acyclic ureas (dimethylimidazoline), sulfoxides and sulfones (dimethyl sulfoxide, dimethyl sulfone, tetramethylene sulfoxide, tetramethylene sulfone) and alcohols (methanol, ethanol, propanol, butanol, ethylene glycol monomethyl ether, ethylene glycol monoethyl ether, diethylene glycol monomethyl ether), nitromethane and water. It is also possible to use mixtures of at least two solvents.

For the purposes of the invention, TM8 metals are transition metals from the group consisting of Cu, Ag, Au, Ni, Co, Rh, Pd, Ir, Ru and Pt. Preferred metals are rhodium and iridium and also ruthenium, platinum and palladium.

Particularly preferred metals are ruthenium, rhodium and iridium.

Depending on the oxidation number and coordination number of the metal atom, the metal complexes can contain further ligands and/or anions. They can also be cationic metal complexes. The ligands can be monodentate or bidentate nonionic or anionic ligands.

Monodentate nonionic ligands can, for example, be selected from the group consisting of olefins (for example ethylene, propylene), allyls (allyl, 2-methallyl), solvating solvents (nitriles, linear or cyclic ethers, unalkylated or N-alkylated amides and lactams, amines, phosphines, alcohols, carboxylic esters, sulfonic esters), nitrogen monoxide and carbon monoxide.

Monodentate anionic ligands can, for example, be selected from the group consisting of halide (F, Cl, Br, I), pseudohalide (cyanide, cyanate, isocyanate) and anions of carboxylic acids, sulfonic acids and phosphonic acids (carbonate, formate, acetate, propionate, methylsulfonate, trifluoromethylsulfonate, phenylsulfonate, tosylate), acetylacetonates.

Bidentate nonionic ligands can, for example, be selected from the group consisting of linear or cyclic diolefins (for example hexadiene, cyclooctadiene, norbornadiene), dinitriles (malononitrile), unalkylated or N-alkylated diamides of carboxylic acids, diamines, diphosphines, diols, dicarboxylic diesters and disulfonic diesters.

Bidentate anionic ligands can, for example, be selected from the group consisting of the anions of dicarboxylic acids, disulfonic acids and diphosphonic acids (for example oxalic acid, malonic acid, succinic acid, maleic acid, methylenedisulfonic acid and methylenediphosphonic acid).

The ligands can also be arenes or heteroarenes (for example benzene, naphthalene, methylbenzene, xylene, cumene, 1,3,5-mesitylene, pyridine, biphenyl, pyrrole, benzimidazole).

Cationic metal complexes can contain anions such as $Cl^-$, $Br^-$, $I^-$, $ClO_4^-$, $CF_3SO_3^-$, $CH_3SO_3^-$, $HSO_4^-$, $BF_4^-$, $B(phenyl)_4^-$, $B(C_6F_5)_4^-$, $B(3,5-bistrifluoromethylphenyl)_4^-$, $PF_6^-$, $SbCl_6^-$, $AsF_6^-$ or $SbF_6^-$.

Metal complexes which are preferably used as component a) are those of the formulae:

$[M(diene)_2]X$, $[M(ene)_2A]_2$, $[M(diene)A]_a$, $[M(diene)L_2]X$, $[ML_bA]$ and $[RuCl_2B)]_2$, $[RuL_3A]X$, $[Ru(diene)(carboxylate)_2]_2$, where M is Rh or Ir, diene is a linear or cyclic diolefin preferably having from 6 to 12 carbon atoms, ene is an olefin preferably having from 2 to 6 carbon atoms, X is an anion selected from the group consisting of $BF_4^-$, $PF_6^-$, $SbF_6^-$, $CH_3COO^-$, $CF_3COO^-$, $CH_3SO_3^-$ and $CF_3SO_3^-$, A is an anionic ligand selected from the group consisting of cyclopentadienyl, substituted cyclopentadienyl, acetylacetonate, tetramethylheptanedionate, hydride and chloride, a is 0 or 1, b is 2, 3 or 4, L is an uncharged ligand selected from the group consisting of CO, $CH_3CN$, PhCN, DMSO, pyridine, substituted pyridine and $PR_3$, where R is alkyl, substituted alkyl, aryl, substituted aryl, heteroaryl or substituted heteroaryl, carboxylate is the salt of a lower $C_1$-$C_6$-carboxylic acid, and B is benzene or alkyl-substituted benzene.

Substituents for pyridine, alkyl, aryl, and heteroaryl are, for example, $C_1$-$C_4$-alkyl, $C_1$-$C_4$-alkoxy, F or Cl.

Metal complexes which are particularly preferably used as component a) are: $[Rh(COD)_2]X$, $[Rh(NBD)_2]X$, $[Ir(COD)_2]X$, $[Ir(NBD)_2]X$, $[Ru(benzene)Cl_2]_2$, $[Ru(1,3,5-triisopropylbenzene)Cl_2]_2$, $[Ru(1,3,5-trimethylbenzene)Cl_2]_2$, $[Ru(p-cymene)Cl_2]_2$, $[Ru(hexamethylbenzene)Cl_2]_2$, $[Ru(hexamethylbenzene)Cl_2]_2$, $[Ru(methallyl)_2(diene)]_2$, $RuCl_3 \cdot xH_2O$, $[RuCl_2(diene)]_n$, $[Ru(DMSO)_4Cl_2]$, $[Ru(PPh_3)H_2(CO)]$, $[Ru(PPh_3)_2 CpCl]$, $[RuCp(CO)_2]_2$, $[Ru(PPh_3)Cl_2]$, $[Ru(PPh_3)_3Cl_2]$, $Ru(acac)_2$ and $Ru(diene)acac_2$, where X can be $BF_4^-$, $PF_6^-$, $SbF_6^-$ or $CF_3SO_3^-$, and COD is 1,5-cyclooctadiene and NBD is norbornadiene.

The phosphine radicals of the diphosphine of the component b) can correspond to the formula —$PR_aR_b$, where $R_a$, $R_b$ are either monovalent hydrocarbon radicals or the two hydrocarbon radicals together with the P atom can form a 3- to 8-membered ring. The hydrocarbon radicals can be unsubstituted or substituted and can contain from 1 to 22, preferably from 1 to 12, carbon atoms. Among these compounds, particular preference is given to those in which the two radicals $R_a$ and $R_b$ are identical and are selected from the group consisting of linear or branched $C_1$-$C_{12}$-alkyl; unsubstituted or $C_1$-$C_6$-alkyl or $C_1$-$C_6$-alkoxy-substituted $C_5$-$C_{12}$cycloalkyl and $C_5$-$C_{12}$-cycloalkyl-$CH_2$—; phenyl and benzyl; and phenyl or benzyl substituted by halogen (for example F, Cl or Br), $C_1$-$C_6$-alkyl, $C_1$-$C_6$-haloalkyl (for example trifluoromethyl), $C_1$-$C_6$-alkoxy, $C_1$-$C_6$-haloalkoxy (for example trifluoromethoxy), $(C_6H_5)_3Si$, $(C_1$-$C_{12}$-alkyl$)_3Si$, secondary amino or $CO_2$—$C_1$-$C_6$-alkyl (for example —$CO_2CH_3$).

The phosphine groups can also be groups of the formulae

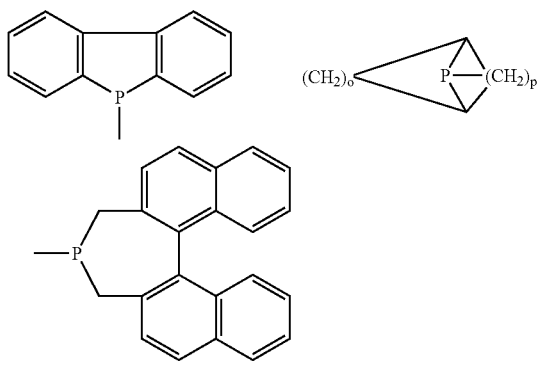

where o and p are each, independently of one another, an integer from 2 to 10 and the sum of o+p is from 4 to 12, preferably from 5 to 8, and the phenyl rings are unsubstituted or substituted by $C_1$-$C_4$-alkyl or $C_1$-$C_4$-alkoxy. Examples are [3.3.1]- and [4.2.1]-phobyl groups of the formulae

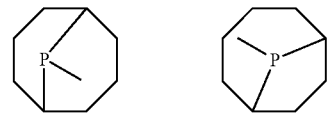

Examples of alkyl substituents on P, which preferably contain from 1 to 6 carbon atoms, are methyl, ethyl, n-propyl, i-propyl, n-butyl, i-butyl, t-butyl, and the isomers of pentyl and hexyl. Examples of unsubstituted or alkyl-substituted cycloalkyl substituents on P are cyclopentyl, cyclohexyl, methylcyclohexyl and ethylcyclohexyl, and dimethylcyclohexyl. Examples of alkyl-, alkoxy-, haloalkyl-, haloalkoxy-substituted phenyl and benzyl substituents on P are methylphenyl, dimethylphenyl, trimethylphenyl, ethylphenyl, methylbenzyl, methoxyphenyl, dimethoxyphenyl, trifluoromethylphenyl, bistrifluoromethylphenyl, tristrifluoromethylphenyl, trifluoromethoxyphenyl, bistrifluoromethoxyphenyl, dimethylaminophenyl, 3,5-di-t-butyl-phen-1-yl, 3,5-di-t-butyl-4-methoxyphen-1-yl, 3,5-di-t-butyl-4-dimethylaminophen-1-yl, 3,5-di-i-propylphen-1-yl, 3,5-di-i-propyl-4-methoxyphen-1-yl, 3,5-di-i-propyl-4-dimethylaminophen-1-yl, 3,5-dimethyl-4-methoxyphen-1-yl, 3,5-di-methyl-4-dimethylaminophen-1-yl and 3,4,5-trimethoxyphen-1-yl.

Preferred phosphine groups —$PR_aR_b$ are ones in which the radicals $R_a$ and $R_b$ are identical and are selected from the group consisting of $C_1$-$C_6$-alkyl, unsubstituted cyclopentyl and cyclohexyl and cyclopentyl and cyclohexyl substituted by from 1 to 3 $C_1$-$C_4$-alkyl or $C_1$-$C_4$-alkoxy groups, benzyl; and in particular phenyl which is unsubstituted or substituted by from 1 to 3 $C_1$-$C_4$-alkyl, $C_1$-$C_4$-alkoxy, $(C_1$-$C_4$-alkyl$)_2$N—, F, Cl, $C_1$-$C_4$-fluoroalkyl or $C_1$-$C_4$-fluoroalkoxy.

The phospholane group can correspond to the formula

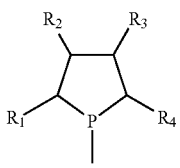

and is preferably in the form of an essentially pure enantiomer. $R_1$ to $R_4$ preferably have the meanings indicated below.

The carbon chain having from 2 to 4 carbon atoms can be, for example, $C_2$-$C_4$-alkylene or -alkenylene, 1,2-arylene, 1,2-heteroarylene, 1,2-cycloalkylene, 1,2-heterocycloalkylene, 1,1'-bisarylene or 1,1'-bisheteroarylene. Examples are ethylene, 1,2- or 1,3-propylene, 1,2-, 1,3- and 1,4-butylene, 1,4-butenylene, 1,3-cylopentylene, 1,2-cyclohexylene, 3,4-pyrrolidinylene or -furanylene or -thienylene, 1,2-phenylene, 1,2-pyrridylene, 1,2-naphthylene, 1,1'-biphenylene and 1,1'-binaphthylene.

The haloalkyl, halocycloalkyl and haloaryl can contain one or more halogen atoms and can be perhalogenated radicals. The halogen is preferably Cl and very particularly preferably F. Particular preference is given to perfluorinated radicals. Some examples are trichloroethyl, pentachloroethyl, trifluoromethyl, pentafluoroethyl and pentafluorophenyl.

$R_c$ is particularly preferably $C_1$-$C_4$-perfluoroalkyl.

Preferred anions are $CF_3COO^-$, $CF_3SO_3^-$, $BF_4^-$, $PF_6^-$, $AsF_6^-$ and $SbF_6^-$.

The component b) used is preferably a phospholane salt of the formula (I) or (II):

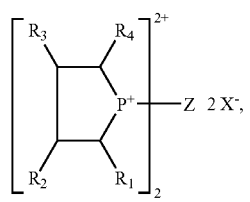

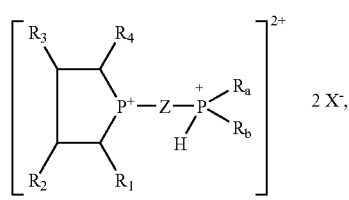

where $R_1$=$R_4$ and are each OH, alkyl, aryl, aralkyl, alkoxy, aryloxy or aralkyloxy;

$R_2$ and $R_3$ are each, independently of one another, H, OH, alkyl, aryl, aralkyl, alkoxy, aryloxy or aralkyloxy, but preference is given to $R_2$=$R_3$; or $R_2$ and $R_3$ together form part of a cycloaliphatic, cycloheteroaliphatic, aromatic or heteroaromatic ring;

$R_a$, $R_b$ are each, independently of one another, a monovalent hydrocarbon radical which has from 1 to 22 carbon atoms and is unsubstituted or substituted, or the two hydrocarbon radicals together with the P atom can form a 3- to 8-membered ring;

Z is a chain comprising from 2 to 4 carbon atoms which may be part of a 1,2-aryl, 1,2-heteroaryl, 1,2-cycloalkyl, 1,2-heterocycloalkyl ring or a 1,1'-bisarylene or 1,1'-bisheteroarylene; and $X^-$ is an anion $R_cCOO^-$, $R_cSO_3^-$, where $R_c$=$C_{1-4}$-alkyl, $C_{5-10}$-cycloalkyl, or $C_{6-10}$-aryl, in each case substituted by halogen atoms, $BF_4^-$, $PF_6^-$, $AsF_6^-$, $SbF_6^-$, $B(C_6F_5)_4^-$ or $B(3, 5$-bistrifluoromethylphenyl$)_4^-$.

In the case of the radicals $R_1$ to $R_4$, alkyl is preferably a $C_{1-4}$-alkyl radical (methyl, ethyl, n-propyl, i-propyl, n-butyl, i-butyl and t-butyl); aryl is preferably phenyl or fused phenyl, aralkyl is preferably an aromatic ring having any substitution pattern and a directly bound alkyl chain, preferably benzyl;

alkoxy is preferably methoxy, ethoxy, propoxy, or i-propoxy;

aryloxy is preferably phenoxy; and aralkyloxy is preferably benzyloxy.

In the case of Z heteroaryl is preferably any aromatic N—, O— or S-heterocycle, which may also be fused with phenyl; and heterocycloalkyl is preferably any aliphatic or partially unsaturated N—, O— or S-heterocycle.

The radicals $R_1$ to $R_4$ can be substituted, for example by $C_1$-$C_4$-alkyl, $C_1$-$C_4$-alkoxy, F or Cl.

The component b), viz. a phospholane of the formula (I) or (II), is preferably one in which $R_1$=$R_4$=methyl, ethyl, i-propyl, or phenyl; and $R_2$=$R_3$=H, OH, methoxy, ethoxy, propoxy, i-propoxy, or benzyloxy; or $R_2$ and $R_3$ are part of an aromatic, heteroaromatic, aliphatic or heteroaliphatic ring.

Compounds which are particularly preferred as component b) are those of the formula (I) containing the abovementioned radicals.

Very particularly preferred components b) are compounds of the formulae (I.1a), (I.1b), (I.2) and (II.1) and their enantiomers:

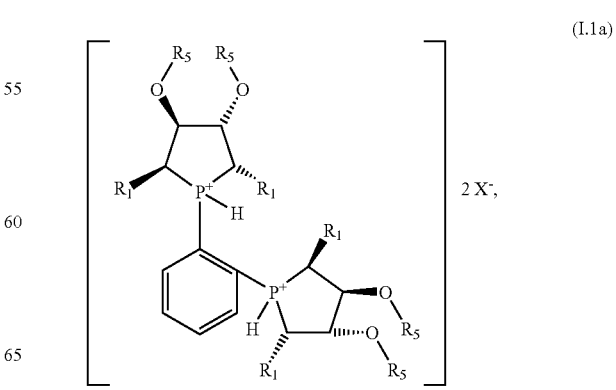

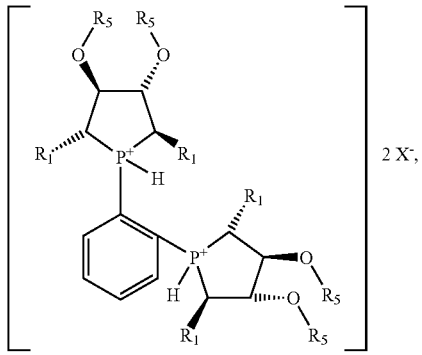

(I.1b)

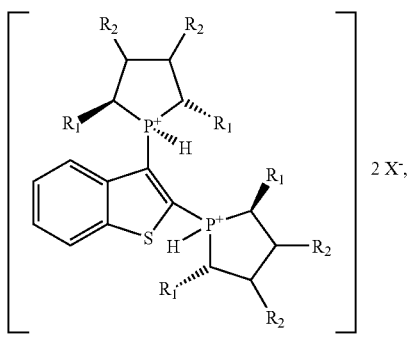

(I.2)

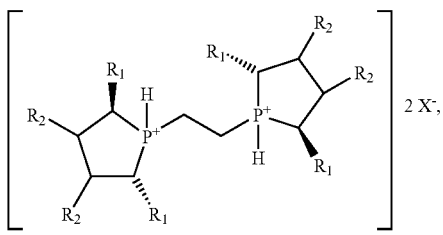

(II.1)

where $R_1$, $R_2$ and $X^-$ have the meanings given above for the formulae (I) and (II), including the preferences and embodiments mentioned there; and $R_5$ is methyl, ethyl, propyl, or i-propyl.

Very particularly preferred components b) also include compounds of the formulae (I.4) and (I.5) and their enantiomers:

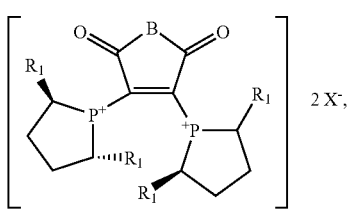

(I.4)

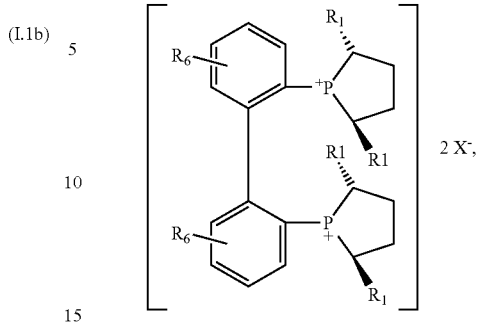

(I.5)

where $R_1$, $R_2$, and $X^-$ have the meanings given above for the formula (I), including the preferences and embodiments mentioned there;

B is $NR_7$ or O, where $R_7$=alkyl, substituted or unsubstituted; aryl, substituted or unsubstituted; aryl, aralkyl, substituted or unsubstituted; heteroaryl, substituted or unsubstituted; cycloalkyl, substituted or unsubstituted; heterocycloalkyl, substituted or unsubstituted, and $R_6$ is H or a fused-on aryl, heteraryl, cycloalkyl or heterocycloalkyl ring; or alkyl, substituted or unsubstituted; alkoxy; aryl, substituted or unsubstituted; $NR_7$, where $R_7$ is as defined above; OH or halogen. In the case of substitution, possible constituents are, for example, $C_1$-$C_4$-alkyl or $C_1$-$C_4$-alkoxy.

Further very particularly preferred compounds used as component b) are the following phospholane salts: 1,2-bis[(2S,3S,4S,5S)-3,4-dihydroxy-2,5-dimethylphospholanyl]benzene bistriflate, 1,2-bis[(2R,3S,4S,5R)-3,4-dihydroxy-2,5-dimethylphospholanyl]benzene bistriflate, and their enantiomers, bis[(2R,5R)-2,5-dimethylphospholanyl]ethane bistetrafluoroborate and its enantiomers.

The anions $X^-$ required for phospholane salt formation are preferably the anions $R_cSO_3^-$, where $R_c$=$C_{1-4}$-alkyl, $C_{5-10}$-cycloalkyl or $C_{6-10}$-aryl, in each case substituted by fluorine atoms, preferably perfluorinated, $BF_4^-$, $PF_6^-$, $SbF_6^-$ or $BArF^-$ (tris(pentafluorophenyl)borate). The best-known example of a perfluorinated anion $RSO_3^-$ is $CF_3SO_3^-$ (triflate).

Preferred anions are $CF_3SO_3^-$, $BF_4^-$, $PF_6^-$, $SbF_6^-$ or $BArF^-$, in particular $CF_3SO_3^-$, $BF_4^-$ and $PF_6^-$.

As adds $H^+X^-$ it is possible to use all acids which have a sufficient acid strength for the respective phospholane.

The catalyst solutions prepared as described above can be used directly for the enantioselective asymmetric hydrogenation of heteroatom-carbon and C=C-double bonds.

The present invention therefore also provides for the use of a catalyst solution prepared according to the invention for the enantioselective asymmetric hydrogenation of heteroatom-carbon and C=C double bonds.

The invention also provides a process for hydrogenating heteroatom-carbon and C=C-double bonds of prochiral organic compounds using metal complexes comprising TM8 metals and ditertiary diphosphines which have one or two phospholane groups bound to a carbon chain having from 2 to 4 carbon atoms as homogeneous hydrogenation catalysts, which is characterized in that the catalyst is prepared in situ prior to the hydrogenation by reacting a) an uncharged or cationic metal complex having a TM8 metal as central atom and b) a salt of a chiral ditertiary diphosphine containing one or two phospholane groups which are bound to a carbon chain having from 2 to 4 carbon atoms and contain anions selected from the group consisting of $R_cCOOR^-$, $R_cSO_3^-$, $BF_4^-$, $PF_6^-$, $AsF_6^-$, $SbF_6^-$, $B(C_6F_5)_4^-$ and $B(3,5\text{-bistrifluoromethylphenyl})_4^-$, with one another, where the ratio of the components a) and b) is from 1:1 to 1:2 and $R_c$ is $C_1$-$C_6$-haloalkyl, $C_5$-$C_{10}$-halocycloalkyl or $C_6$-$C_{10}$-haloaryl.

A further advantage of the invention is that the phospholanes used as component b) for the preparation of a catalyst solution are air-stable when particular anions are chosen. Here, air-stable is defined as follows: the substance, viz. the phospholane salt, is not sensitive to oxidation and no decomposition occurs under normal laboratory conditions (storage at 20-30° C. and 40% relative atmospheric humidity) within the first 12 hours after isolation of the salt. Furthermore, the salts according to the present invention are not hygroscopic or only moderately hygroscopic. The latter are advantageously stored under protective gas. The long-term stability of the salts according to the invention can be checked by no optical changes (visual examination), mechanical changes (the powder flow of the solid does not deteriorate) and analytical changes (comparison of the NMR spectrum with that of the initial state) occurring after a particular period of time after preparation of the salt, for example 4 weeks.

The invention further provides the phospholane salts of the formula (III) or (IV) used as intermediates in the form of substantially pure enantiomers:

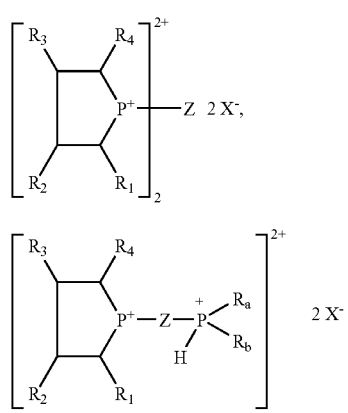

where the radicals $R_1$ to $R_4$, $R_a$, $R_b$, Z and $X^-$ have the meanings given under the abovementioned formulae (I) and (II), with the proviso that the compound 1,2-bis(2,5-dimethylphospholanyl)benzene tetrafluoroborate is excluded.

The same preferences and embodiments as indicated above for the formulae (I) and (II) apply to the phospholane salts of the invention.

The phospholane salts of the formulae (III) and (IV) can be prepared by generally known methods, according to which the phosphene is dissolved in an organic solvent which is stable towards acids, e.g. methanol, chloroform and the like, and admixed at room temperature with a slight excess of about 1.1 equivalents of acid per phosphorus function.

After evaporation of the solvent and purification of the solid obtained in this way, the phospholane salts are obtained as virtually analytically pure powders.

As mentioned above, the phospholane salts of the invention can function as ligands in the in-situ preparation of catalyst solutions. To prepare these catalyst solutions, an on-site user can advantageously make use of a kit comprising two containers of which one container contains a TM8 metal complex as such or in solution while the other container contains a phospholane salt according to the invention either as such or in solution. The same preferences and embodiments as mentioned above for the TM8 metal complexes and the phospholane salts of the invention apply to a kit according to the invention.

The present invention therefore further provides a kit comprising two containers of which one container contains a TM8 metal complex as such or in solution and the other container contains a phospholane salt according to the invention either as such or in solution.

In the use of phospholane ligands for homogeneous catalysts, the in-situ process of the invention offers considerable advantages over preformed metal complexes. It is not necessary to take any particular protective measures in order to avoid decomposition of sensitive phospholanes. The phospholane salts are so stable that they can be stored and transported without problems. The catalysts or catalyst precursors prepared in situ create stable hydrogenation conditions. These advantages make possible the industrial use of phospholanes as ligands in metal complexes which can be prepared by the user immediately prior to the hydrogenation.

The following examples illustrate the invention.

Preparation of Salts

EXAMPLE A1

1,2-Bis[(2S,3S,4S,5S)-3,4-dihydroxy-2,5-dimethylphospholanyl]benzene bistriflate 500 mg (1.1 mmol) of 1,2-bis[(2S,3S,4S,5S)-3,4-isopropylidene-2,5-dimethylphospholanyl]benzene are suspended in 2 ml of methanol and 0.5 ml of water. The mixture is cooled to 0° C. and 200 µl (2.25 mmol) of trifluoromethanesulfonic acid are added dropwise, giving a clear solution. This is stirred at room temperature for 15 minutes and the solvent is then taken off into a cold trap. The residue is dried by azeotropic evaporation with benzene, which gives 620 mg (83% of theory) of the title compound as an air-stable, nonhygroscopic, white powder.

$^1$H NMR: 0.86 (dd, 6H); 1.30 (dd, 6H); 2.94-3.12 (m, 2H); 3.18-3.34 (m, 2H); 4.06-4.24 (m, 4H); 7.66-7.78 (m, 2H); 8.02-8.18 (m, 2H)

$^{31}$P NMR: 10.6 (bs)

Analysis calculated for $C_{20}H_{30}F_6O_{10}P_2S_2$: C: 35.83; H: 4.51; S: 9.56; found: C: 35.37; H: 4.36; S: 9.59.

EXAMPLE A2

1,2-Bis[(2S,3S,4S,5S)-3,4-dihydroxy-2,5-dimethylphospholanyl]benzene bishexafluorophosphate 500 mg (1.11 mmol) of 1,2-bis[(2S,3S,4S,5S)-3,4-isopropylidene-2,5-dimethylphospholanyl]benzene are suspended in 2 ml of methanol and 0.5 ml of water. The mixture is cooled to 0° C. and 517 µl (2.30 mmol) of hexafluorophosphoric acid (65% aqueous) are added dropwise, giving a clear yellowish solution. This is stirred at room temperature for 15 minutes and the solvent is then taken off into a cold trap. The residue is dried by azeotropic evaporation with benzene, which gives 690 mg (94% of theory) of the title compound as an air-stable, nonhygroscopic, white powder.

$^1$H NMR: 0.87 (dd, 6H); 1.32 (dd, 6H); 2.95-3.17 (m, 2H); 3.20-3.38 (m, 2H); 4.00-4.25 (m, 4H); 7.67-7.82 (m, 2H); 8.03-8.18 (m, 2H)

$^{31}$P NMR: −143.0 (Septet, PF$_6$); 11.0 (bs)

Analysis calculated for C$_{18}$H$_{30}$F$_{12}$O$_4$P$_4$: C: 32.64; H: 4.57; P: 18.71; found: C: 32.68; H: 4.67; P: 18.1.

EXAMPLE A3

Bis[(2R,5R)-2,5-dimethylphospholanyl]ethane bistetrafluoroborate 200 mg (0.77 mmol) of bis[(2R,5R-2,5-dimethylphospholanyl]ethane are dissolved in 2 ml of methanol. The solution is cooled to 0° C. and 221 µl (2.30 mmol) of tetrafluoroboric acid (50% aqueous) are added dropwise, whereupon the formation of a white precipitate is observed. The solvent is taken off into a cold trap and the solid obtained is washed with THF. The remaining water is removed by azeotropic evaporation with benzene, giving 390 mg (90%) of the title compound as an air-stable, nonhygroscopic, white powder.

$^1$H NMR: 1.18-1.32 (2× dd, 12H); 1.40-1.62 (m, 4H); 1.85-2.25 (m, 8H); 2.30-2.60 (m, 4H)

$^{31}$P NMR: 23.0 (bs)

Analysis calculated for C$_{14}$H$_{30}$B$_2$F$_8$P$_2$: C: 38.75; H: 6.97; P: 14.28; found: C: 38.67; H: 6.81; S: 14.3.

In the case of 1,2-bis(2,5-dimethylphospholanyl)ethane (BPE, corresponding to the abovementioned formula (II.1) with R$_1$=methyl and R$_2$=H), formation of the bistetrafluoroborate the salt converts a liquid, extremely oxidation-sensitive substance into a completely stable solid. This does not adversely affect the enantiomeric purity of the ligand concerned.

EXAMPLE A4

1,2-Bis[(2S,3S,4S,5S)-3,4-dihydroxy-2,5-dimethylphospholanyl]benzene bistetrafluoroborate 5 g (11.10 mmol) of 1,2-bis[(2S,3S,4S,5S)-3,4-isopropylidene-2,5-dimethylphospholanyl]benzene are suspended in 50 ml of methanol and 10 ml of water. The mixture is cooled to 0° C. and 2.8 ml (22.20 mmol) of tetrafluoroboric acid (50% aqueous) are added dropwise and the mixture is refluxed for 30 minutes. The resulting clear solution is evaporated and the residue is dried by azeotropic evaporation with benzene, which gives 5.7 g (94% of theory) of the title compound as a moderately hygroscopic, white powder.

$^1$H NMR: 0.87 (dd, 6H); 1.32 (dd, 6H); 3.03-3.18 (m, 2H); 3.22-3.38 (m, 2H); 4.06-4.20 (m, 4H); 7.70-7.80 (m, 2H); 8.05-8.18 (m, 2H)

$^{31}$P NMR: 10.9 (bs)

EXAMPLE A5 (COMPARATIVE EXAMPLE)

1,2-Bis[(2S,3S,4S,5S)-3,4-dihydroxy-2,5-dimethylphospholanyl]benzene bismesylate 6 g (13.32 mmol) of 1,2-bis[(2S,3S,4S,5S)-3,4-isopropylidene-2,5-dimethylphospholanyl]benzene are suspended in 120 ml of methanol and 6 ml of water. 1.8 ml (27.97 mmol) of methanesulfonic acid are added dropwise and the mixture is refluxed. The initial suspension becomes clear during the course of the reaction. After 30 minutes the solvent is taken off into a cold trap and the resulting white powder is washed with diethyl ether. It is dried by azeotropic evaporation with benzene, which gives 4.1 g (86% of theory) of the title compound as a highly hygroscopic white powder.

$^1$H NMR: 0.86 (dd, 6H); 1.31 (dd, 6H); 3.00-3.15 (m, 2H); 3.20-3.36 (m, 2H); 4.06-4.22 (m, 4H); 7.68-7.78 (m, 2H); 8.06-8.17 (m, 2H)

$^{31}$P NMR: 10.9 (bs)

This comparative example of a methanesulfonate (mesylate) salt according to the abovementioned paper by Zhang, X. et al is highly hygroscopic. A choice of tetrafluoroborate (experiment A4) gives a moderately hygroscopic salt, while the analogous salts obtained when triflate (experiment A1) or hexafluorophosphate (experiment A2) is chosen in each case make it possible to obtain a nonhygroscopic, very stable form of the ligand.

A) Use Examples

EXAMPLE B1

Catalytic Hydrogenation of Dimethyl Itaconate Using 1,2-bis[(2S,3S,4S,5S)-3,4-dihydroxy-2,5-dimethylphospholanyl]benzene Bistriflate A glass autoclave provided with a magnetic stirrer bar is charged with the ligand from Example A1 (2.78 mg, 4.15× 10$^{-6}$ mmol), evacuated to a high vacuum and filled with argon, with this operation being repeated three times. Solutions of [Rh(norbornadiene)$_2$]BF$_4$ (0.74 ml, 3.0 M, 3.95×10$^{-6}$ a mmol in methanol), dimethyl itaconate (1.25 ml, 0.79 mmol, 0.63 M in methanol) and triethylamine (1.3 ml, 4.7× 10$^{-2}$ mmol, 3.6×10$^{-2}$ M in methanol) are added in succession while stirring. The mixture is briefly placed under vacuum and argon is admitted. This procedure is subsequently repeated three times more using hydrogen (1.1 bar) instead of argon and the mixture is stirred for one hour.

The reaction mixture (clear, yellow solution) is evaporated on a rotary evaporator. Gas chromatography (Lipodex E, 50 cm×0.25 mm, 190 kPa H$_2$, 80° C. isothermal) of an aliquot indicates that conversion is quantitative and an enantiomeric excess of 99.8% (R) is achieved.

The invention claimed is:

1. A process for preparing a catalyst solution which comprises reacting metal complexes and diphosphines in the presence of an inert organic solvent, wherein
   a) an uncharged or cationic metal complex having a TM8 metal as central atom, and
   b) a salt of a chiral ditertiary diphosphine which has one or two phospholane groups which are bound to a carbon chain having from 2 to 4 carbon atoms and contain anions selected from the group consisting of R$_c$COO$^-$, R$_c$SO$_3^-$, BF$_4^-$, PF$_6^-$, AsF$_6^-$, SbF$_6^-$, B(C$_6$F$_5$)$_4^-$ and B(3, 5-bistrifluoromethylphenyl)$_4^-$, are reacted with one another, where the ratio of the components a) and b) is from 1:1 to 1:2,
   R$_c$ is C$_1$-C$_6$-haloalkyl, C$_5$-C$_{10}$-halocycloalkyl or C$_6$-C$_{10}$-haloaryl, and
   wherein the metal complex used as component a) corresponds to one of the formulae:

[M(diene)$_2$]X, [M(ene)$_2$A]$_2$, [M(diene)A]$_a$, [M(diene) L$_2$]X, [MIL$_b$A] and [RuCl$_2$B)]$_2$, [RuL$_3$A]X, [Ru (diene)(carboxylate)$_2$]$_2$, wherein M is Rh or Ir, diene is a linear or cyclic diolefin, ene is an olefin, X is an anion selected from the group consisting of $BF_4^-$, $PF_6^-$, $SbF_6^-$, $C_3COO^-$, $CF_3COO^-$, $CH_3SO_3^-$ and $CF_3SO_3^-$, A is an anionic ligand selected from the group consisting of cyclopentadienyl, substituted cyclopentadienyl, acetylacetonate, tetramethylheptanedionate, hydride and chloride, a is 0 or 1, b is 2, 3 or 4, L is an uncharged ligand selected from the group consisting of CO, $CH_3CN$, PhCN, DMSO, pyridine, substituted pyridine and $PR_3$, where R is alkyl, substituted alkyl, aryl, substituted aryl, heteroaryl or substituted heteroaryl, carboxylate is the salt of a lower $C_1$-$C_8$-carboxylic acid, and B is benzene or alkyl-substituted benzene, and wherein the component b) is a phospholane salt of the formula (I) or (II):

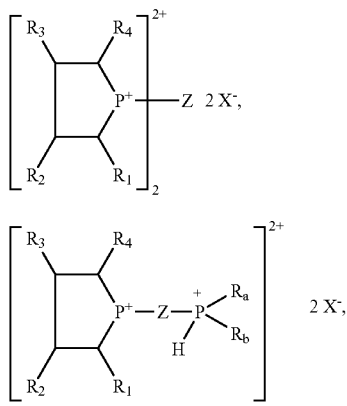

wherein $R_1=R_4$ and are each OH, alkyl, aryl, aralkyl, alkoxy, aryloxy or aralkyloxy;

$R_2$ and $R_3$ are each, independently of one another, H, OH, alkyl, aryl, aralkyl, alkoxy, aryloxy or aralkyloxy; or $R_2$ and $R_3$ together form part of a cycloaliphatic, cycloheteroaliphatic, aromatic or heteroaromatic ring;

$R_a$, $R_b$ are each, independently of one another, a monovalent hydrocarbon radical which has from 1 to 22 carbon atoms and is unsubstituted or substituted, or the two hydrocarbon radicals together with the P atom can form a 3- to 8-membered ring;

Z is a chain comprising from 2 to 4 carbon atoms which may be part of a 1,2-aryl, 1,2-heteroaryl, 1,2-cycloalkyl, 1,2-heterocycloalkyl ring or a 1,1'-bisarylene or 1,1'-bisheteroarylene; and $X^-$ is an anion $R_cCOO^-$, $R_cSO_3^-$, where $R_c=C_{1-4}$-alkyl, $C_{5-10}$-cycloalkyl, or $C_{6-10}$aryl, in each case substituted by halogen atoms, $BF_4^-$, $PF_6^-$, $AsF_6^-$, $SbF_6^-$, $B(C_6F_5)_4^-$ or $B(3,5\text{-bistrifluoromethylphenyl})_4^-$, with the proviso that the compounds 1,2-bis(2,5-dimethylphospholanyl)benzene tetrafluoroborate and 1,2-bis(2,5-dimethylphospholanyl)benzene bistetrafluoroborate are excluded.

2. A process according to claim 1, wherein diene is a linear or cyclic diolefin having from 6 to 12 carbon atoms, ene is an olefin having from 2 to 6 carbon atoms, and $R_2=R_3$.

3. A process according to claim 1, wherein the component b) is a phospholane salt of the formula (I.1a), (I.1b), (I.2) or (II.1) or an enantiomer thereof:

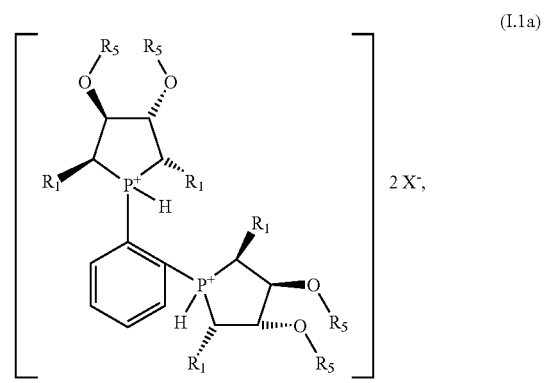

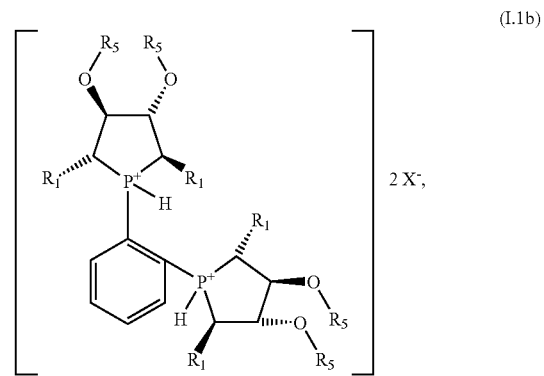

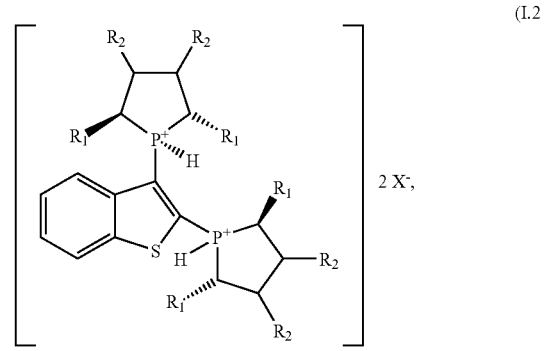

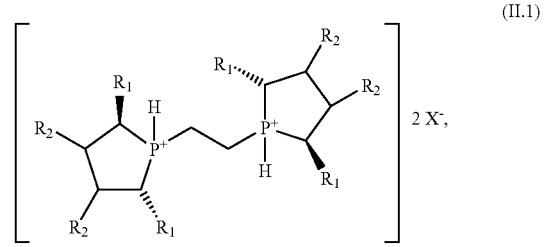

wherein $R_1$, $R_2$ and $X^-$ are as defined in claim 1 and $R_5$ is methyl, ethyl, propyl or i-propyl.

4. A process according to claim 1, in which the anion required for phospholane salt formation is selected from the anions $R_cSO_3^-$, wherein $R_c$=$C_{1-4}$-alkyl, $C_{5-10}$-cycloalkyl or $C_{6-10}$-aryl, in each case substituted by fluorine atoms, $BF_4^-$, $PF_6^-$, $SbF_6^-$ or $BArF^-$.

5. A process according to claim 4, wherein $R_c$ is perfluorinated $C_{1-4}$-alkyl, perfluorinated $C_{5-10}$-cycloalkyl or perfluorinated $C_{6-10}$-aryl.

6. A phospholane salt of formula (III) or formula (IV):

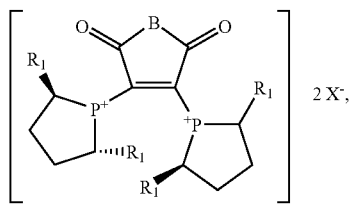 (1.4)

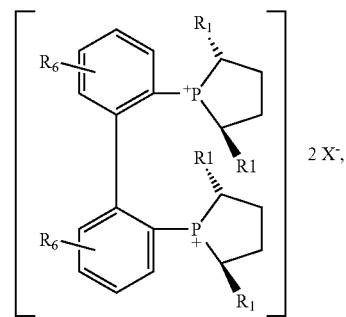 (1.5)

wherein
the radicals $R_1$ to $R_4$, $R_a$, $R_b$, Z and $X^-$ have the meanings given in claim 1 for the formulas (I) and (II), with the proviso that the compounds 1,2-bis(2,5-dimethylphospholanyl)benzene tetrafluoroborate and 1,2-bis(2,5-dimethylphospholanyl)benzene bistetrafluoroborate are excluded.

7. A phospholane salt selected from the group consisting of 1,2-bis[(2S,3S,4S,5S)-3,4-dihydroxy-2,5-dimethylphospholanyl]benzene bistriflate, 1,2-bis[(2R,3S,4S,5R)-3,4-dihydroxy-2,5-dimethylphospholanyl]benzene bistriflate and their enantiomers, bis[(2R,5R)-2,5-dimethylphospholanyl]ethane bistetrafluoroborate and its enantiomers.

* * * * *

UNITED STATES PATENT AND TRADEMARK OFFICE
CERTIFICATE OF CORRECTION

| | | |
|---|---|---|
| PATENT NO. | : 7,491,671 B2 | Page 1 of 2 |
| APPLICATION NO. | : 10/556084 | |
| DATED | : February 17, 2009 | |
| INVENTOR(S) | : Kesselgruber et al. | |

It is certified that error appears in the above-identified patent and that said Letters Patent is hereby corrected as shown below:

Delete column 15 and column 16 in its entirety and in insert column 15 and column 16 as shown on the attached page.

Signed and Sealed this
Twenty-seventh Day of March, 2012

David J. Kappos
*Director of the United States Patent and Trademark Office*

4. A process according to claim 1, in which the anion required for phospholane salt formation is selected from the anions $R_cSO_3^-$, wherein $R_c=C_{1-4}$-alkyl, $C_{5-10}$-cycloalkyl or $C_{6-10}$-aryl, in each case substituted by fluorine atoms, $BF_4^-$, $PF_6^-$, $SbF_6^-$ or $BArF^-$.

5. A process according to claim 4, wherein $R_c$ is perfluorinated $C_{1-4}$-alkyl, perfluorinated $C_{5-10}$-cycloalkyl or perfluorinated $C_{6-10}$-aryl.

6. A phospholane salt of formula (III) or formula (IV):

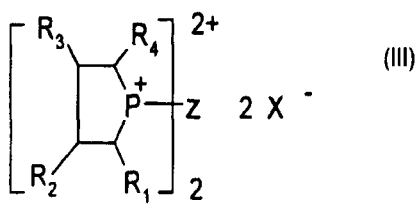
(III)

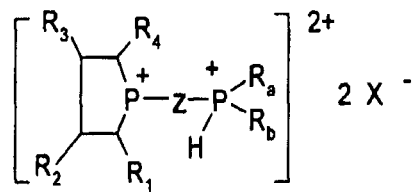
(IV)

wherein
the radicals $R_1$ to $R_4$, $R_a$, $R_b$, Z and $X^-$ have the meanings given in claim 1 for the formulas (I) and (II), with the proviso that the compounds 1,2-bis(2,5-dimethylphospholanyl)benzene tetrafluoroborate and 1,2-bis(2,5-dimethylphospholanyl)benzene bistetrafluoroborate are excluded.

7. A phospholane salt selected from the group consisting of 1,2-bis[(2S,3S,4S,5S)-3,4-dihydroxy-2,5-dimethylphospholanyl]benzene bistriflate, 1,2-bis[(2R,3S,4S,5R)-3,4-dihydroxy-2,5-dimethylphospholanyl]benzene bistriflate and their enantiomers, bis[(2R,5R)-2,5-dimethylphospholanyl]ethane bistetrafluoroborate and its enantiomers.

* * * * *